United States Patent
Hoang et al.

(10) Patent No.: US 9,926,558 B2
(45) Date of Patent: Mar. 27, 2018

(54) CULICINAE MOSQUITO TRA-2 RNA INTERFERENCE TECHNIQUE TO GENETICALLY PRODUCE MALENESS POPULATION

(76) Inventors: Duong Thanh Hoang, Hanoi (VN); Kim Phuc Hoang, Oxford (GB)

( * ) Notice: Subject to any disclaimer, the term of this patent is extended or adjusted under 35 U.S.C. 154(b) by 453 days.

(21) Appl. No.: 14/356,978

(22) PCT Filed: Dec. 29, 2011

(86) PCT No.: PCT/VN2011/000011
§ 371 (c)(1),
(2), (4) Date: May 8, 2014

(87) PCT Pub. No.: WO2012/129577
PCT Pub. Date: Sep. 27, 2012

(65) Prior Publication Data
US 2014/0331342 A1    Nov. 6, 2014

(30) Foreign Application Priority Data

Mar. 23, 2011    (VN) .............................. 1-2011-00772

(51) Int. Cl.
*C12N 15/113*    (2010.01)
*C12N 15/85*    (2006.01)
*A01K 67/033*    (2006.01)

(52) U.S. Cl.
CPC ........ *C12N 15/113* (2013.01); *A01K 67/0333* (2013.01); *A01K 67/0339* (2013.01); *A01K 2217/058* (2013.01); *A01K 2227/706* (2013.01); *A01K 2267/02* (2013.01); *C12N 2310/14* (2013.01); *C12N 2330/51* (2013.01)

(58) Field of Classification Search
USPC ....... 435/6.1, 91.1, 9, 1.31, 320.1, 455, 375, 435/91.31; 536/23.1, 24.5; 800/13, 21
See application file for complete search history.

(56) References Cited

U.S. PATENT DOCUMENTS

2003/0213005 A1    11/2003    Alphey
2009/0183269 A1*    7/2009    Alphey .............. A01K 67/0339
                                                                  800/21

FOREIGN PATENT DOCUMENTS

EP    1246927 A2    10/2002
WO    WO 2001/39599    6/2001
WO    WO 2005/012534    2/2005

OTHER PUBLICATIONS

Wang et al., Cell 127, pp. 803-815, 2006.
Thomas et al., Science, vol. 257, pp. 2474-2476 (2000).
Papathanos et al., Malaria J., 2009, 8 (Suppl 2):S5, pp. 1-8.
Sarno et al., BMC Evolutionary Biology, 2010, 10:140 (14 pages); www.biomedcentral.com/1471-2148/10/140.
Salvemini et al., BMC Evolutionary Biology, 2011, 11:41 (19 pages); www.biomedcentral.com/1471-2148/11/41.
Salvemini et al., Int. J. Dev. Biol., 53:109-120 (2009).
Phuc et al., BMC Biology, 2007, 5:11 (11 pages); www.biomedcentral.com/1741-7007/5/11.
Hammond et al., Nature, Reviews, vol. 2, 2001, pp. 110-119.
Gossen et al., PNAS USA, vol. 89, pp. 5547-5551 (1992).
Gong et al., Nature Biotech., 2005 vol. 23, No. 4, pp. 453-456.
Fu et al., PNAS, vol. 107, No. 10, pp. 4550-4554 (2010).
Fortier et al., Genesis 26:240-244 (2000).
Database, GenBank, , XM_001648781, Jan. 31, 2009, Retrived from the Internet: <UR:http:/blast.ncbi.nlm.nih.gov/Blast.cgi>.
Database, GenBank, XM_ 001866676, Dec. 1, 2009, Retrived from the Internet: <IJRL:http:/blast.ncbi.nlm.nih.gov/Blast.cgi>.
International Search Report, dated Mar. 20, 2012, from International Phase of the instant application.
Salvenimi, et al., Ceratitis capitata transformer-2 gene . . . female sex determination, Int.J.Dev,Biol. 2009 (abstract), 53:109-120.
Lobo, et al., Germ line transformation of the yellow fever mosquito . . . piggyBac vector, Insect Mol. Biol. 2002 (abstract), 11(2):133-139.
Michiels, et al., A 14 bp promoter element directs . . . Drosophila beta 2 tubulin gene, EMBO J., 1989 (abstract), 8(5):1559-1565.
Daffa'Alla, T., et al., Use of regulatory mechanism of sex determination in pest insect control, Journal of Genetics, 2010, 89(3):301-305.

* cited by examiner

*Primary Examiner* — Jane Zara
(74) *Attorney, Agent, or Firm* — Nosh and Titus, LLC

(57) ABSTRACT

The present invention develops a novel method for controlling mosquito populations. Culicinae mosquitoes carrying one or more loci of transformant Tra-2 RNAi constructs which target to mosquito Transformer-2 locus in respective or none respective Culicinae mosquitoes. Tra-2 sequences used to assemble Tra-2 RNAi recombinant constructs are Tra-2 gene sequences of Culicinae mosquitoes and can be derived from endogenous or exogenous sequences. The Tra-2 RNAi expression is conditional, wherein the expression causing a knockdown effect into the endogenous Tra-2 gene results in mortality of X (m) chromosome bearing sperms and produces maleness mosquito population in the nature environmental of the species.

5 Claims, 1 Drawing Sheet

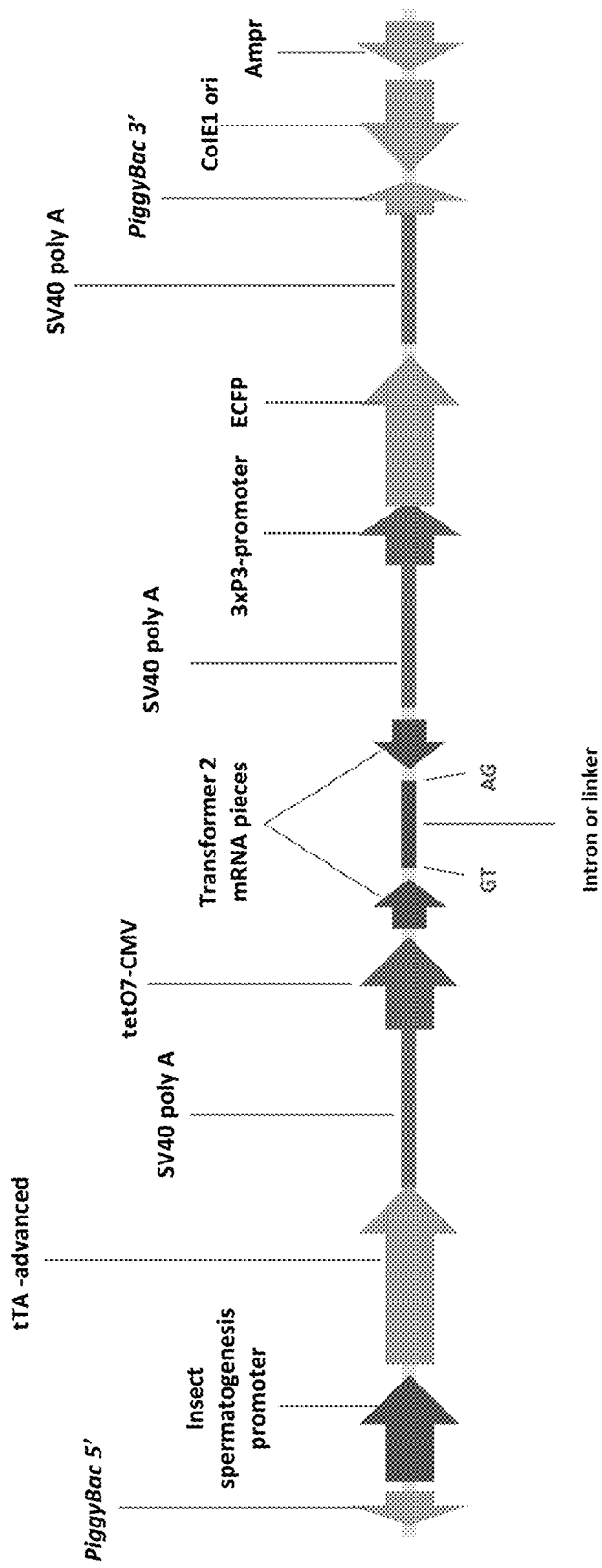

CULICINAE MOSQUITO TRA-2 RNA INTERFERENCE TECHNIQUE TO GENETICALLY PRODUCE MALENESS POPULATION

FIELD OF THE INVENTION

The present invention relates to the field of molecular biology to develop a novel method for controlling mosquito populations. Culicinae mosquitoes carrying one or more loci of transformant Tra-2 RNAi constructs which target to mosquito Transformer-2 locus in respective or none respective Culicinae mosquitoes. Tra-2 sequences used to assemble Tra-2 RNAi recombinant constructs are Tra-2 gene sequences of Culicinae mosquitoes and can be derived from endogenous or exogenous sequences. The Tra-2 RNAi expression is conditional, wherein the expression causing a knockdown effect into the endogenous Tra-2 gene results in mortality of X (m) chromosome bearing sperms and produces maleness mosquito population in the nature environmental of the species.

BACKGROUND OF THE INVENTION

Nowadays, there are many biological control techniques have been invented for controlling insects and plants (Smith and Borstel, 1972. *Science*. 178. 1164-1174). A method invented to control of insect populations is named the "sterile insect technique" SIT. This method is also known with a different name as "sterile insect release method" SIRM. A model of the SIRM based on population parameters obtained from a large scale experiment to eradicate melon fly was first developed by Ito (1977. *Appl. Ent. Zool.* 12:310-312; 1979. *Res. Popul. Ecol.* 20. 216-226). The SIT method creates sterile male insects and releases them into natural habitats where the males would look for natural females to mate. These females would be sterile or to produce offspring that cannot develop up to the harmful stages. When a huge number of sterile males released in a chronic time, it can cause a collapse of the natural insect populations or even extinction. However, the insect created by the SIT method need to be undergone a sexing step to remove females. The reason is that in many insect species, even sterile females, if being released, they would look for blood meals and may transmit diseases (in mosquitoes) or damage fruits (in med fly). As such, release of the female insects must be avoided.

Currently, there are different methods to separate male insects from a total based on the differences of sexual traits as body sizes or eclosion time. However, systematic errors of those are high and more or less depending on each species, for instance, our data indicated that 8-15% females of *Aedes aegypti* mosquitoes can be misidentified as males (K. P. Hoang, unpublished data). Alternatively, insects can be frozen down on ice to separate females and males. However, this method is too high labor costs and can damage small insects as male mosquitoes.

In another approach, X and gamma rays are used to translocate a chromosome fragment which carries genes encoding for different colors of silk worm male and female eggs (Strunnikov, 1979. *Theor. Appl. Genet.* 55, 17-21; Strunnikov. 1983. *Control of silkworm Reproduction, Development and Sex*. MIR Publishers. Moscow). However, the mutant strains created by radiation are usually accompanied with a significant decline in male mating competitiveness in comparison with its wild type males. This can result in failures in vector control strategies if applying for the release of insect males. Besides, irradiation method is not specific to the certain target, the radiation not only causes big mutations in chromosome systems of the target organisms but can also be dangerous for producers. This is also an expensive method with plenty of limitations.

Asburner et al., (1998) disclose a method by introduction of an exogenous DNA fragment into the insect genetic system to create insect transgenic species (*Insect Molecular Biology*, 7 (3), 201-213). This approach was lately improved by a patent of Handler (2006. PN: U.S. Pat. No. 7,005, 296B1).

DeVault disclose to use a female specific promoter to be ligated into a lethal gene. The gene is only activated in females and therefore males are uniquely remained in the selection. These males are irradiated for sterilization before releasing into nature (DeVault et al., 1996; *Biotechnology*, Vol 14; 46-49; DeVault et al., 1996. *Genome Res.* 6: 571-579). This achievement gains a big progress in the genetic sexing experiments, however the use of radiation can severely damage for small insects with its consequences of decreasing male mating competitiveness ability.

To avoid the radiation damages, a new method named RIDL (Release of Insects carrying a dominant lethal) has been disclosed in a patent (Alphey, 1999. PN: WO 01/39599 A2; Alphey, 2007. *Area-Wide Control of Insect Pests: From Research to Field Implementation*, Springer, Dordrecht, The Netherlands). The RIDL offers a solution to many of the drawbacks of traditional SIT that have limited its application in mosquitoes as mentioned above. RIDL differs from conventional SIT in that the released insects are not sterilized by irradiation but its sterility is resulted from a homozygote for a dominant lethal gene. Highly efficient repressible RIDL systems were first demonstrated in *Drosophila* models and recently in the Mediterranean fruit fly (Thomas et al., 2000. *Science*, 287: 2474-2476; Gong et al., 2000. *Nature Biotech.*, 23: 453-456.). This system exploits a tetracycline-repressible transactivator (tTA) to control expression of the dominant lethal (Gossen and Bujard, 1992. *Proc Natl Acad Sci USA* 1992, 89(12):5547-5551). The tetracycline (Tet) that to be mixed in larval rearing medium or food can bind to tTA and preventing it binding to tetO sequences and driving the effector gene. The tetO sequences plays a role of an operator would be free to suppress the lethal gene. In the absence of Tet, tTA protein binds to the operator sequence and the effector gene would be free to express. In natural environment where Tet is absent, released transgenic males mates with wild type females and their offspring would be killed by the effector gene activation. In *Aedes* mosquitoes, RIDL has been proved to be efficient, of which the males created haven't been declined their fitness when competing with wild type males. (Phuc et al., 2007; *BMC Biology* http://www.biomedcentral.com/1741-7007/5/11). However, the RIDL method has a serious shortcoming that it still produces offspring in both sexes. It therefore needs an addition step of sexing to remove females before releasing.

Fu et al., (2010. *PNAS*, Vol. 107, No. 10, 4550-4554) discloses a method in which a fusion between RIDL system and a female sex-specific regulation based on an endogenous Actin-4 promoter that derived from *Aedes aegypti* females. The effector gene is specifically activated only in the direct-flight muscle of female mosquitoes and this expression makes females to be flightless. These females after eclosion would be stuck on the water surface and to be dead eventually. By this method, only 50% of offspring becomes males which can continuously pass the transformant genetic systems into next generation. However, this method in practice has a shortcoming. This happens when plenty of the flightless females staying on the water surface, their bodies and leg movements can prevent other eclosion males to come up with the water which may eventually drown males. The higher rearing density is the higher "collateral damage" for males, but in industrial insectary, rearing at high density is the only option.

Transformer-2 gene has been seen as a key factor in combination with Tra for sex determination in different eukaryotes although it may involve differently in different taxa depending on evolutionary divergence. Fortier and Belote (2000. *Genesis* 26(4): 240-244), Salvemini et al (2009. *Int. J. Dev. Biol.* 53: 109-120) and Sarno et al (2010. http://www.biomedcentral.com/1471-2148/10/140) used the RNAi method to knock down the Tra-2 genes in *Drosophila, Ceratitis Capitata* and *Anastrepha*, respectively. The knockdown effect can convert females of these species into pseudo males carrying XX chromosomes. In their studies, the RNA interference method is performed by injection of Tra-2 double stranded RNA (dsRNA) into embryos after an invitro synthesized step.

No tra-2 orthologue has been identified in *Anopheles* and the Tra-2 orthologue in *Aedes aegypti* mosquitoes seems to involve in a different genetic mode. A full length mRNA transcription of Tra-2 gene in *Aedes aegypti* is not necessarily required for its downstream gene cascade, doublesex (dsx) to be spliced. One female specific Dsx can be default spliced to be females (Salvemini et al., 2011. *BMC Evolutionary Biology* 2011, 11:41 http://www.biomedcentral.com/1471-2148/11/41). It, therefore, suggests that the wish to create all maleness offspring, including 50% pseudo [XX (mm)] males by a conversion from females is impossible if targeting Tra-2 in Culicinae. In fact, in our experiments, Tra-2 dsRNA injection into Culicinae mosquito eggs hasn't caused a significant bias in sex ratio.

The present invention sets out to overcome all the shortcoming of the previous methods by using the common principles of the RIDL method (Alphey, 1999. PN: WO 01/39599 A2; Alphey, 2007. *Area-Wide Control of Insect Pests: From Research to Field Implementation*, Springer, Dordrecht, The Netherlands) in combination with a discovery of X (m) bearing sperm killing effect due to Tra-2 RNAi genetic system. These transgenic Culicinae mosquitoes are therefore to produce more than 90% genetic maleness offspring.

BRIEF DESCRIPTION OF THE FIGURE

FIG. 1 describes RNAi kernel sequences controlled by a regulatory element in a transactivator system within a PiggyBac plasmid. This a is diagrammatic representation of a completed Tra2-RNAi system, linearized at the 3' end of the piggyBac transposon. There are three functional segments within the ends of the transposon: the marker (3×P3 promoter-ECFP-SV40 poly A3') to allow detection of transgenic individuals by fluorescence. tTA protein is under the control of an insect spermatogenesis promoter (*Drosophila* β2) and terminated by a SV40 poly A 3' sequence. The third segment is the Tra-2 Rnai cassette (tetO7-CMV minimal promoter—two Tra2 mRNA inverted repeats joined by a fragment of a linker or intron sequence. This is also terminated by a SV40 poly A 3' sequence. The Tra-2 Rnai cassette acts by a tTA protein binding into the tetO7 in the absence of Tetra cycline to free CMV minimal promoter to drive.

SUMMARY AND TECHNIQUE PRINCIPLES OF THE INVENTION

We discovered that is not like the Tra-2 in *Drosophila, Ceratitis Capitata* and *Anastrepha*, the Tra-2 gene in Culicinae mosquitoes is involved in male specific, spermatogenesis processes and the knockdown of Tra-2 gene hasn't resulted in a conversion from females to males as occurred in the other Dipteran insects. Because, a transient effect of dsRNA cannot last from eggs to adults to consistently cause a knockdown effect into spermatogenesis stages and following consequences in next generation, therefore all attempts to use dsRNA injections to obtain transient effects would be invalid.

To successfully repress the Tra-2 gene in mosquitoes, it is necessary to create permanent transgenic lines with Tra-2 RNAi constructs by which the interference effect will be stably expressed during the spermatogenesis stages. We found that Tra-2 gene knockdown in Culicinae mosquitoes can cause lethality of X (m) chromosome bearing sperms and therefore only Y-chromosome (M) bearing sperms are survival and maleness offspring would be produced. These males are genetic males which carry a Y chromosome. Males created by this method are not sterile but they produce healthy Y chromosome bearing sperms only. Theoretically, maleness offspring would continuously pass the Tra-2 RNAi constructs into natural populations until the populations gone extinct.

This invention discloses all of the methods to create Tra-2 RNAi DNA constructs, to transform it into mosquitoes and to observe its expression.

The invention uses putative Transformer-2 encoding gene sequences from *Aedes albopictus, Aedes polynesiensis, Culex quinquefasciatus* or the other Culicinae mosquitoes as materials to assemble Tra-2 RNAi genetic constructs by using DNA recombination techniques. In Examples of this invention, parts or whole RRM (RNA recognition motif) sequences which are belonging to putative Transformer-2 encoding sequences from *Aedes albopictus, Aedes polynesiensis* and *Culex quinquefasciatus* are used.

The Tra-2 of *Aedes aegypti* is identified by blasting against the *Aedes aegypti* Genbank database with an input is the *Drosophila* Tra-2A amino acid sequence. The outcome was AAEL004293-RA protein belonging to supercontig 1.113 (*Aedes aegypti*-Vectorbase). *Aedes aegypti* are closely related species with *Aedes albopictus* and *Aedes polynesiensis*, therefore primers derived from the AAEL004293-RA sequence can be used to amplify Tra-2 sequences of *Aedes albopictus* and *Aedes polynesiensis* mosquitoes. The regions with highest similarity among the orthologous Tra-2 genes are RRMs (RNA recognition motives) with a length of 240 bp. For many other *Aedes* spp these primers were tested and can successfully amplify these 240 bp regions. We found two RRMs loci (or allele), each exists in both *Aedes albopictus* and *Aedes polynesiensis*. They are different 10% amino acid from each other and named as SEQ ID: No 1 (RRM1) and SEQ ID: No 2 (RRM2). To knock down these two loci (allele), it may be required to transform two respective RNAi constructs into each species to repress the respective RRM locus (allele).

A putative Tra-2 gene of *Culex quinquefasciatus* is identified by blasting *Culex quinquefasciatus* database with the RRM1 and RRM2 sequences. The name of the outcome is CPIJ016646; supercontig 3.780:5008-5247. The RRMs of *Culex* orthologous Tra-2 gene is named as SEQ ID: No 3 (RRM3). For many other *Culex* spp, primers derived from the first and the end of the RRM3 region have been tested and can successfully amplify these 240 bp regions.

In order to knock down the Tra-2 genes in *Aedes albopictus, Aedes polynesiensis, Culex quinquefasciatus* and the other Culicinae mosquitoes by the RNAi technique, there are three solutions to be disclosed in the invention.

The first solution is to use SEQ ID: No 1 (RRM1) as materials to invitro create an RNAi kernel sequence 1. This is a recombinant DNA fragment combining two identical sequences of RRM1 but in opposite directions. A connection between the two RRM1 repeats is a straight intron or linker DNA sequence. The RNAi kernel sequence 1 is then ligated with transactivator and regulatory elements and a fluorescent marker within a PiggyBack plasmid. This plasmid would then be available for transforming into both *Aedes albopictus* and *Aedes polynesiensis* to knock down their RRM1 locus.

The regulatory element for the kernel sequence is a minimal promoter associated with operator sequences (tetOx7). The minimal promoter plus tetOx7 can be conditional by using the commercial transactivator regulation systems (Clontech). Gene expression is activated as a result of binding of the Tet-Off protein (tTA) to tetracycline response elements (TREs) located within the minimal promoter.

For the best of expression, the invention suggests to use insect spermatogenesis specific promoters to control tTA protein gene. Besides, we also prefer to derive a minimal promoter from an insect spermatogenesis specific promoter for controlling the RNAi kernel sequence 1 which helps to eliminate all leakiness effect. This solution may be applied for any other *Aedes* spp which has a highly similar sequence of its RRM in comparison with the RMM1 or after obtaining its own Tra-2 RRM sequences by the same pair of primers.

The second solution is to use SEQ ID: No 2 (RRM2) as materials to invitro create an RNAi kernel sequence 2. This is a recombinant DNA fragment combining two identical sequences of RRM2 but in opposite directions. A connection between the two RRM2 repeats is a straight intron or linker DNA sequence. The RNAi kernel sequence 2 is then ligated with regulatory elements and a fluorescent marker within a piggyBack plasmid. This plasmid would then be available for transforming into both *Aedes albopictus* and *Aedes polynesiensis* to knock down their RRM2 locus.

In the details, the regulatory elements in the second solution are identical as those described in the first solution.

This solution may be applied for any other *Aedes* spp which has a highly similar sequence of its RRM in comparison with the RMM2 or after obtaining its own Tra-2 RRM sequences by the same pair of primers.

The third solution is to use SEQ ID: No 3 (RRM3) as materials to invitro create a RNAi kernel sequence 3. This is a recombinant DNA fragment combining two identical sequences of RRM3 but in opposite directions. A connection between the two RRM3 repeats is a straight intron or linker DNA sequence. The RNAi kernel sequence 3 is then ligated with regulatory elements and a fluorescent marker within a piggyBack plasmid. This plasmid would then be available for transforming into *Culex quinquefasciatus*.

In the details, the regulatory elements in the third solution are identical as those described in the first and second solutions. This solution can be applied for any other *Culex* spp which has a highly similar sequence of its RRM in comparison with the RMM3 or after obtaining its own Tra-2 RRM sequences by a pair of primers to be mentioned in Examples.

The connective intron or linker between two Tra-2 RRM inverted repeats can be any eukaryote intron sequence. However, introns from the respective species are preferred. The length of connective linker or intron can be from few to few hundred nucleotides. We prefer that two nucleotides of GT and AG need to be inserted at the beginning and at the end of intron or linker, respectively. These are the strengthening signals for spliceosomes to recognize and to splice out the connective introns or linkers.

Three DNA Tra-2 RNAi RRM-1, Tra-2 RNAi RRM-2, Tra-2 RNAi RRM-3 kernel sequences are disclosed here as examples of using specifically Tra-2 DNA sequences to produce an interference effect into the respective species. The transcription of the DNA kernel structure containing two identically inverted repeats would produce single strands of mRNAs, which exposes two complementary sequences at its two ends. The complementary sequences would bind together forming a double strand hairpin mRNA structure (dsRNAi), in which the looping part is formed by the intron or linker. Mosquito cells recognize the abnormal structure and react by dicing the dsRNA interference in a defend mechanism activity which is followed by destroying intact single strand Tra-2 mRNAs from itself (Wang et al., 2006. *Cell* 127, 803-815; Hammond et al., 2001. *Nat Rev Genet.* 2(2):110-9). The Tra-2 gene is, therefore, knocked down.

Illustrations and its Explanations

| The RNAi kernel sequences 1. | | |
|---|---|---|
| Tra-2 RRM RNAi- 1 | | |
| Forward sequence | Connection | Reverse sequence |
| 5'AGTAAGTGCCTCGGTGTGTTCGGCCTAAGC<br>AGCTACACCAACGAAACCAGCCTGATGGACG<br>TTTTCGCACCGTACGGAACCATTGACAAGGC<br>GATGATTGTCTACGATGCCAAGACGAAGGTT<br>TCCCGNGGGTTCGGATTCGTGTACTTCCAGG<br>AGCAGAGTGCGGCCACCGAAGCCAAAATGCA<br>GTGYAATGGNATGATGCTGCATGAGCGCACG<br>ATTAGAGTGGATTATTCGGTGACC-3'<br>(SEQ ID NO: 1) | | |
| | GT-Intron-AG<br>(or<br>linker) | 5'GGTCACCGAATAATCCACTCTAATCGTG<br>CGCTCATGCAGCATCATNCCATTYCACTGC<br>ATTTTGGCTTCGGTGGCCGCACTCTGCTCC<br>TGGAAGTACACGAATCCGAACCCNCGGGAA<br>ACCTTCGTCTTGGCATCGTAGACAATCATC<br>GCCTTGTCAATGGTTCCGTACGGTGCGAAA<br>ACGTCCATCAGGCTGGTTTCGTTGGTGTAG<br>CTGCTTAGGCCGAACACACCGAGGCACTTA<br>CT-3' (SEQ ID NO: 4) |

The RNAi kernel sequences 1.

The respective amino acid sequence (SEQ ID NO: 5)

```
 1 -S--K--C--L--G--V--F--G--L--S--S--Y--T--N--E--T--S--L--M--D-

21 -V--F--A--P--Y--G--T--I--D--K--A--M--I--V--Y--D--A--K--T--K-

41 -V--S--R--G--F--G--F--V--Y--F--Q--E--Q--S--A--A--T--E--A--K-

61 -M--Q--C--N--G--M--M--L--H--E--R--T--I--R--V--D--Y--S--V--T-
```

Note:
3' end of the forward sequence is connected with an intron or linker sequence by GT. 5' end of reverse sequence is connected with the intron or linker sequence by AG. The bold italicized characters indicate substitutions. Y, S, N, K etc show different possibilities of changed nucleotides at the same position. The substitutions may or may not change amino acid code.

The RNAi kernel sequences 2.

Tra-2 RRM RNAi-2

| Forward sequence | Connection | Reverse sequence |
|---|---|---|
| 5'AGTAAGTGCCTCGGTGTGTTCGGCCT*N* AG *Y*AGCTA*Y*ACCA*M*CGAA*R*CCA*R*CCTGATGGA*Y* GT*N* TT*CK CN* CCGT*W*GG*N* ACCAT*H*GACAAGG C*N* ATGATTGTCTACGATGCCAAGACGAAGG*Y N* TCCCG*N* GGGTT*Y*GG*N* TTCGTGTA*Y*TTCCAG GAGCAGAGT*K*CGGCCAC*N* GA*R*GCCAAA*M*TGC AGTG*Y*AA*Y*GGAATG*RWR*CTGCA*Y*GAGCG*N* AC GATTAGAGTGGATTATTCGGTGACC-3' (SEQ ID NO: 2) | GT-Intron-AG (or linker) | 5'GGTCACCGAATAATCCACTCTAATCGT*N* CGCTC*Y*TG CA*GRWR*CATTCC*Y*TT*Y*CACTGCA*M*TTTGGC*R*TC*N* GTGG CC*GK*ACTCTGCTCCTGGAA*Y*TACACGAA*N* CC*Y*AACCC*N* CGGGA*NY*CCTTCGTCTTGGCATCGTAGACAATCAT*N* GC CTTGTC*H*ATGGT*N* CC*GW*ACGG*N* G*K*GAA*N* AC*Y*TCCATCA GG*R*TGG*R*TTC*GM*TGGT*Y* TAGCT*Y* CT*N* AGGCCGAACACA CCGAGGCACTTACT-3' (SEQ ID NO: 6) |

The respective amino acid sequence (SEQ ID NO: 7)

```
 1 -S--K--C--L--G--V--F--G--L--S--S--Y--T--*T*--E--T--*N* --L--M--D-

21 -V--F--S--P--*F*--G--T--I--D--K--A--M--I--V--Y--D--A--K--T--K-

41 -A--S--R--G--F--G--F--V--Y--F--Q--E--Q--S--*S*--A--T--E--A--K-

61 -*L*--Q--C--N--G--M--*E*--L--H--E--R--T--I--R--V--D--Y--S--V--T-
```

Note:
3' end of the forward sequence is connected with an intron or linker sequence by GT. 5' end of reverse sequence is connected with the intron or linker sequence by AG. The bold italicized characters indicate substitutions. Y, S, N, K etc show different possibilities of changed nucleotides at the same position. The substitutions may or may not change amino acid code.

The RNAi kernel sequences 3.

Tra-2 RRM RNAi-3

| Forward sequence | Connection | Reverse sequence |
|---|---|---|
| 5'CGTAACGGAATAGTCCACCCGGATGGTT CGCTCGTGCATTACCATTCCGTTGCACTGC ACCTTGGCTGCGGAAGCGTCCTCCAGGTTG ACAAAGTACACGAATCCGAACCCGCGGGAC GCCTTCGTCTTGGCATCGTACACGATCTGC ACCTTCTCGATCAATCCGAACCGGCCAAAC ACGGTCCTCAGGTCCGCCTCCTGGGTGTAA | | |

-continued

The RNAi kernel sequences 3.

```
TTGCTGAGGCCAAACACGCCGAGGCAGGTC
GA-3' (SEQ ID NO: 3)
```

| | |
|---|---|
| GT-Intron-AG (or linker) | 5'TCGACCTGCCTCGGCGTGTTTGGCCTCAGC AATTACACCCAGGAGGCGGACCTGAGGACCGT GTTTGGCCGGTTCGGATTGATCGAGAAGGTGC AGATCGTGTACGATGCCAAGACGAAGGCGTCC CGCGGGTTCGGATTCGTGTACTTTGTCAACCT GGAGGACGCTTCCGCAGCCAAGGTGCAGTGCA ACGGAATGGTAATGCACGAGCGAACCATCCGG GTGGACTATTCCGTTACG-3' (SEQ ID NO: 8) |

The respective amino acid sequence (SEQ ID NO: 9)

```
 1  -S--T--C--L--G--V--F--G--L--S--N--Y--T--Q--E--A--D--L--R--T-
21  -V--F--G--R--F--G--L--I--E--K--V--Q--I--V--Y--D--A--K--T--K-
41  -A--S--R--G--F--G--F--V--Y--F--V--N--L--E--D--A--S--A--A--K-
61  -V--Q--C--N--G--M--V--M--H--E--R--T--I--R--V--D--Y--S--V--T-
```

Note:
3' end of the forward sequence is connected with an intron or linker sequence by GT. 5' end of reverse sequence is connected with the intron or linker sequence by AG. The bold italicized characters indicate substitutions. Y, S, N, K etc show different possibilities of changed nucleotides at the same position. The substitutions may or may not change amino acid code.

Sequence ID Number.
SEQ ID: No 1 RRM1
5'AGTAAGTGCCTCGGTGTGTTCGGCCTAAGCAGC-TACACCAACGAAACCAGCCTGATGG ACGTTTTCG-CACCGTACGGAACCATTGACAAGGCGATGATTGTC-TACGATGCCAAGACGA
AGGTTTCCCGNGGGTTCGGATTCGTGTACTTCCAG-GAGCAGAGTGCGGCCACCGAAGCC AAAATGCAGT-GYAATGGNATGATGCTGCATGAGCGCACGATTA-GAGTGGATTATTCGGTG ACC-3'
SEQ ID: No 2 RRM2
5'AGTAAGTGCCTCGGTGTGTTCGGCCTNAG-YAGCTAYACCAMCGAARCCARCCTGATGG
AYGTNTTCKCNCCGTWCGGNACCATHGACAAGGC-NATGATTGTCTACGATGCCAAGACG AAGGYNTC-CCGNGGGTTYGGNTTCGTGTAYTTCCAGGAGCA-GAGTKCGGCCACNGARGC
CAAAMTGCAGTGYAAYGGAATGRWRCTGCAY-GAGCGNACGATTAGAGTGGATTATTCGG TGACC-3'
SEQ ID: No 3 RRM3
CGTAACGGAATAGTCCACCCGGATGGTTCGCTCGT-GCATTACCATTCCGTTGCACTGCAC CTTGGCTGCG-GAAGCGTCCTCCAGGTTGACAAAGTACACGAATC-CGAACCCGCGGGACG
CCTTCGTCTTGGCATCGTACACGATCTGCACCT-TCTCGATCAATCCGAACCGGCCAAACA CGGTC-CTCAGGTCCGCCTCCTGGGTGTAATTGCTGAGGC-CAAACACGCCGAGGCAGGTC GA.

DETAILED DESCRIPTION OF THE INVENTION

The Tra-2 RNAi system in the present invention may be any part of Tra-2 encoding sequences (mRNA) of Tra-2 genes originated from *Aedes albopictus, Aedes polynesiensis, Culex quinquefasciatus* or the other Culicinae mosquitoes which are capable of producing a knockdown (interference) effect to the Tra-2 gene of the respective species. We not rule out the possibilities that a Tra-2 RNAi system containing Tra-2 recombinant sequences from a certain Culicinae mosquito species can also cause a knockdown (interference) effect to the other closely related mosquito species within Culicinae.

Definitions

Culicinae mosquitoes refer to mosquito species which have a pair of chromosome (chromosome I) that are similar in size but are distinguishable in many species by the presence in the X (m) or absence in the Y(M) of C-banding intercalary heterochromatin (Knudson et al., 1996. 175-214. *The Biology of Disease vectors*. University Press of Colorado).

Tra-2 gene sequences from Culicinae mosquitoes refer to mRNA coding sequences only (Latchman, 1998. *Gene regulation. A eukaryotic perspective.* 3$^{rd}$ edition. Stanley Thornes Publishers).

The RNAi kernel sequences refer to any recombinant DNA sequence which includes two inverted repeats (IR) in conjunction by a linker or intron sequence. Sequence of the IR is derived from any part of Culicinae Tra-2 mRNA sequences.

We definite that Tra-2 RNAi kernel sequences is an RNAi encoding sequence, its expression is under the control of a repressible transactivator protein system.

As mentioned above, we look for an existence of the Tra-2 genes in *Aedes albopictus, Aedes polynesiensis* and *Culex quinquefasciatus* mosquitoes which may contain a highly conserved region with a length of 240 bp (80 amino acids). This region has been identified in *Drosophila, Ceratitis Capitata* as Tra-2 RRM specific region (RNA recognition motif) http://www.expasy.org/cgi-bin/prosite-search-ac?P-DOC00030.

Using a sequence from 1221182 to 1220943 of *Aedes aegypti* Tra-2 gene (GenBank accession number: AAEL004293-RA), two primers have been designed. A forward is CLF, 26 bp at beginning of the RRM region (AGTAAGTGCCTCGGTGTGTTCGGCCT (SEQ ID NO:

10)) and a reverse is CLR, 23 bp at the end of the RRM region (CCGGTCACCGAATAATCCACTCAA (SEQ ID NO: 11)). PCR products amplified on DNA templates from *Aedes albopictus* and *Aedes polynesiensis* were sequenced. It revealed that in each species there are two different RRM sequences, RRM1 and RRM2. RT-PCR has shown expression from both of those RRMs. RRM1 is identical with the Tra-2 RRM in *Aedes aegypti* (AAEL004293-RA) but RRM2 has 10% amino acid differences. These pair of primers can be used to amplify ortholog Tra-2 RRM 240 bp regions from the other *Aedes* spp, even the distance species as *Aedes niveus, Aedes annandalei* or *Aedes pseudoalbopictus*. The amplification condition is similar.

A Tra-2 sequence of *Culex quinquefasciatus* is available from Genbank (GenBank accession number: CPIJ016646) when using the RRM1 and RRM2 sequence as inputs to blast. Its RRM sequence belongs to the supercontig 3.780, from 5008 to 5247. We named it as RRM3. 24 bp at beginning and 22 bp at the end of RRM3 are used to create a pair of primers to amplify it from *Culex quinquefasciatus* DNA. These pair of primers can be used to amplify ortholog Tra-2 RRM 240 bp regions of the other *Culex* spp, even the distance species as *Culex visnue, Culex pipiens*. The amplification condition is similar.

For convenience in designing primers whole or a part of the RRM regions (RRM1, RRM2 and RRM3) can be used to assemble the Tra-2 RNAi constructs by DNA recombinant techniques. However, in this invention, it doesn't limit to use other Tra-2 encoding parts outside the RRM region of these mosquitoes to build other Tra-2 RNAi constructs.

The elements that regulate the RNAi kernel sequences should be located on the same chromosome as the RNAi kernel sequences. In FIG. 1 shows the RNAi kernel sequences and Tetracycline (Tet) transactivator system. An insect spermatogenesis promoter, for instance *Drosophila* β2, controls the tTA protein gene. In the presence of Tet in larva rearing medium, tTA protein binds to Tet and the operator sequence (tetO7) would bind to the minimal promoter which regulates the transcription of the kernel structure. The promoter is inactivated and no RNAi product is transcribed. In the absence of Tet, this artificial protein binds to operator tetOx7 in the absence of Tetracycline (Tet) and the minimal promoter would be free to transcribe the RNAi strand. In the same plasmid, a reporter gene as ECFP, Dsred2 or EGFP can be ligated to a 3×P3 or Actin5C promoter. We can trace the plasmid by following this fluorescent marker. The entire packet is ligated into a PiggyBac plasmid. This complex can be transformed into mosquito genetic background in one or more loci which can be in the same or different chromosomes.

We suggest that a single locus of the transgene in a transgenic line can be used as a background for another transformation. A second transformant locus which occurs in the same chromosome with the first one, would be particularly preferred. Transformants occurred in the same chromosome would prevent them to be segregated in the next generations and especially in the case where the two Tra-2 loci (or allele) exist in same species as *Aedes albopictus* and *Aedes polynesiensis*, in which two respective RNAi transformants are necessary to repress two loci (or allele).

The expression of the RNAi kernel sequences would knock down the Tra-2 gene in the transgenic species. The knockdown effect results in lethal X chromosome bearing sperms and only male offspring is outcome.

EXAMPLES

Components:
1/RRM Tra-2 sequences: In this examples, we used three types of RRMs (RRM1, RRM2 and RRM3) to create Tra-2 RNAi kernel constructs. These sequences are obtained from sequencing the target species or blasting from (http://www.vectorbase.org/). It doesn't limit to use a different part of the Tra-2 gene sequences which are belonging to *Aedes albopictus, Aedes polynesiensis, Culex quinquefasciatus* or the other Culicinae mosquitoes in the invention. All the other components of plasmids are identical. 2/ *Drosophila* β2 tubulin promoter (or other insect spermatogenesis promoter): PCR from *Drosophila* DNA. 3/ Transactivator component (tTA): Clontech. 4/ Regulator element (tetOx7): Clontech. 5/ Reporter gene: http://piggybac.bio.nd.edu/. 6/ Piggybac plasmids: http://piggybac.bio.nd.edu/. 7/ Helper plasmid: http://piggybac.bio.nd.edu/.

I. RRMs from *Aedes albopictus* and *Aedes polynesiensis*.

These examples show how the RRM sequences of Tra-2 were identified from *Aedes albopictus* and *Aedes polynesiensis*. It also shows the way to create the RNAi kernel sequence by using the RRM sequences from *Aedes albopictus* and *Aedes polynesiensis*.

As mentioned above, RRM regions of *Aedes albopictus* and *Aedes polynesiensis* have been amplified by a PCR used a pair of primers of 26 bp at beginning and 23 bp at the ending of *Aedes aegypti* supercontig 1.113 (1221182-1220943).

```
                                          (SEQ ID NO: 10)
CLF AGTAAGTGCCTCGGTGTGTTCGGCCT (SEQ ID NO: 11)
CLR CCGGTCACCGAATAATCCACTCAA
```

DNA from *Aedes albopictus* and *Aedes polynesiensis* are extracted using a QIAGEN kit. PCR is carried out in 25 µl reaction in a condition of 2.5 µl PCR buffer; 1.5 µl MgCL (25 mM); 0.5 µl dNTPs (10 mM); each primer 0.5 µl (10 pmol/µl); 0.15 µl Taq DNA polymerase (5 U/µl); 10-40 ng DNA template. Thermal profile of PCR is [94° C./4; (94° C./30"; 59° C./30"; 72° C./45")×3; (94° C./30"; 57° C./30"; 72° C./45")×3; (94° C./30"; 54° C./30"; 72° C./45")×35; 72° C./10']. PCR products are then purified and sequenced with the same primers. Two 240 bp sequences of RRMs are obtained below.

```
RRM1 DNA sequence
                                          (SEQ ID NO: 1)
5'AGTAAGTGCCTCGGTGTGTTCGGCCTAAGCAGCTACACCAACGAAACCAGCCTGATGG

ACGTTTTCGCACCGTACGGAACCATTGACAAGGCGATGATTGTCTACGATGCCAAGACGA

AGGTTTCCCGNGGGTTCGGATTCGTGTACTTCCAGGAGCAGAGTGCGGCCACCGAAGCC

AAAATGCAGTGYAATGGNATGATGCTGCATGAGCGCACGATTAGAGTGGATTATTCGGTG
```

-continued

ACC-3'.
Underlined regions disclosed as SEQ ID NOS 10, 12 and 13,
respectively, in order of appearance.

RRM2 DNA sequence
(SEQ ID NO: 2)
5'<u>AGTAAGTGCCTCGGTGTGTTCGGCC</u>TNAGYAGCTAYACCAMCGAARCCARCCTGATGGAYGT

NTTCKCNCCGTWCGNACCATHGACAAGGNATGATTGTCTAC<u>GATGCCAAGACGAAGGYN</u>

<u>TCCCGNGGGTTYGGNTTCGTGTAYTTCCAGGAGCAGAGTKCGGCCACNGARGC

CAAMTGCAGTGYAAYGGAATGRWRCTGCAYGAGCGNACGA</u><u>TTAGAGTGGATTATTCGG

TGACC</u>-3'.
Underlined regions disclosed as SEQ ID NOS 10, 14 and 13,
respectively, in order of appearance.

RRM1 amino acid sequence
(SEQ ID NO: 5)
1 -S--K--C--L--G--V--F--G--L--S--S--Y--T--N--E--T--S--L--M--D-

21 -V--F--A--P--Y--G--T--I--D--K--A--M--I--V--Y--D--A--K--T--K-

41 -V--S--R--G--F--G--F--V--Y--F--Q--E--Q--S--A--A--T--E--A--K-

61 -M--Q--C--N--G--M--M--L--H--E--R--T--I--R--V--D--Y--S--V--T-

RRM2 amino acid sequence
(SEQ ID NO: 7)
1 -S--K--C--L--G--V--F--G--L--S--S--Y--T--*T*--E--T--N--L--M--D-

21 -V--F--*S*--P--*F*--G--T--I--D--K--A--M--I--V--Y--D--A--K--T--K-

41 -*A*--S--R--G--F--G--F--V--Y--F--Q--E--Q--S--*S*--A--T--E--A--K-

61 -*L*--Q--C--N--G--M--*E*--L--H--E--R--T--I--R--V--D--Y--S--V--T-

(Underlines indicate the region selected for primers. Bold italicized characters
indicate nucleotide and amino acid substitutions).

Beside, these pair of primers can be used to amplify this Tra-2 RRM 240 bp region of the other *Aedes* spp, even from the distance species as *Aedes niveus*, *Aedes annandalei* or *Aedes pseudoalbopictus*. Using the same PCR condition, an exact 240 bp band would be amplified among other bands. An agarose gel extraction step is performed for the 240 bp band by Qiagen columns. The DNA elution is diluted between 10-20 times in water and 1 μl to be used as template for the same PCR. A 240 bp specific band would be amplified and can be used to assemble Tra-2 RNAi constructs for the respective species.

Two fragments of 135 bp from the bottom parts of these RRM1 and RRM2 regions are used to assemble Tra-2 RNAi constructs. Because the sequences of RRM1 and RRM2 are only different in some parts, therefore the primers derived outside of those parts can be used for amplifying both RRMs. PCR is carried out in 25 μl reaction in a condition of 2.5 μl PCR buffer; 1.5 μl MgCL (25 mM); 0.5 μl dNTPs (10 mM); each primer 0.5 μl (10 pmol/μl); 0.15 μl Taq DNA polymerase (5 U/μl); 10-40 ng DNA template. Thermal profile of PCR is [94° C./4; (94° C./30"; 59° C./30"; 72° C./45")×3; (94° C./30"; 57° C./30"; 72° C./45")×3; (94° C./30"; 54° C./30"; 72° C./45")×35; 72° C./10']

1-(BA-EX1F)
(SEQ ID NO: 15)
5'CGATCTC<u>GGATCC</u>ATGCCAAGACGAAGGTTTCCCGAG 3'

2-(X-Ex1R)
(SEQ ID NO: 16)
5'CGGCAATGAC<u>CTCGAG</u>ACCGGTCACCGAATAATCCACTCAA 3'

3-(SAL-EX1F)
(SEQ ID NO: 17)
5'GGCGTCAAT<u>GTCGAC</u>ATGCCAAGACGAAGGTTTCCCGAG 3'

4-(ECORI-EX1R)
(SEQ ID NO: 18)
5'CGGACGTTG<u>GAATTC</u>GACGGTCACCGAATAATCCACTCAA 3'

Primers 1 &3 or 2&4 are similar forward and reverse primers. A combination between 1&2 would produce the same PCR product as that of 3&4. The differences in those PCR products are endonuclease restriction enzyme sequences inserted in the front parts of the primers (underline). This allows the PCR products can be ligated to an intron or linker that contains the same restriction sites in a desired direction. If a connection between the two inverted repeats is a linker about 10 bp, PCRs to amplify these fragments can use the same reverse primer (2 or 4) and therefore products would contain the same restriction sites at 3' end (XhoI or EcoRI). Two PCR products would be easily inversely connected after an XhoI or EcoRI enzyme treatments. However, if we want to insert an intron between the two inverted repeats, it needs to use both inverse primers. Two PCR products would then have different sticky ends at 3' (XhoI and EcoRI) and can be easily ligated with an intron that ends by XhoI and EcoRI restriction sites. In this invention, any linker or intron sequence from other insects can be used in conjunction with the two inverted repeats, provided that two nucleotides GT and AG would be inserted at the first and the end of those sequences, respectively. These are recognition signals for intron splicing sites.

After two identical DNA fragments are reversely connected via an intron or linker, these RNAi kernel sequences (1&2) can be easily ligated into the transactivator system in a desired direction provided that the transactivator plasmids contain the same restriction sites.

II. RRM from *Culex quinquefasciatus*

Genomic sequences of *Culex quinquesfaciatus* are available in the Vectorbase.org website (http://www.vectorbase.org/). We used two RRMs (RRM1 and RRM2) as queries to blast against the database. Outcome is a 240 bp sequence which is highly similar with RRM1 and RRM2 in its helix structure as well as phylogenic relationship. RRM3 contains up to 69% and 73% amino acid similarity with RRM1 and RRM2, respectively. The annotation of Tra-2 *Culex quinquesfaciatus* is CPIJ016646; supercont3.780:5008-5247. (RRM3)

```
RRM3 DNA sequence
                                                    (SEQ ID NO: 3)
CGTAACGGAATAGTCCACCCGGATGGTTCGCTCGTGCATTACCATTCCGTTGCACTGCAC

CTTGGCTGCGGAAGCGTCCTCCAGGTTGACAAAGTACACGAATCCGAACCCGCGGGACG

CCTTCGTCTTGGCATCGTACACGATCTGCACCTTCTCGATCAATCCGAACCGGCCAAACA

CGGTCCTCAGGTCCGCCTCCTGGGTGTAATTGCTGAGGCCAAACACGCCGAGGCAGGTC

GA.
Underlined regions disclosed as SEQ ID NOS 19 and 20,
respectively, in order of appearance.

RRM3 amino acid sequence
                                                    (SEQ ID NO: 9)
 1 -S--T--C--L--G--V--F--G--L--S--N--Y--T--Q--E--A--D--L--R--T-

21 -V--F--G--R--F--G--L--I--E--K--V--Q--I--V--Y--D--A--K--T--K-

41 -A--S--R--G--F--G--F--V--Y--F--V--N--L--E--D--A--S--A--A--K-

61 -V--Q--C--N--G--M--V--M--H--E--R--T--I--R--V--D--Y--S--V--T-
(Underlines indicate the region selected for primers).
```

In *Culex quinquesfaciatus* whole RRM3 sequence can be used to create an RNAi kernel sequence as its nucleotide sequences at beginning and at the end are suitable to design good primers. 24 bp at beginning and 22 bp at the end of RRM3 (underline) are used to create a pair of primers. These pair of primers can be used to amplify this Tra-2 RRM 240 bp region of the other *Culex* spp, even the distance species as *Culex vishnue, Culex pipiens* or *Culex tritaeniorhynchus* by a similar condition. Using the same PCR condition, an exact 240 bp band would be amplified among other bands. A gel extraction step is performed for the 240 bp band by Qiagen columns. The DNA elution is diluted between 10-20 times in water and 1 µl to be used as template for the same PCR. A 240 bp specific band would be amplified and can be used to assemble Tra-2 RNAi constructs for the respective species.

```
7-(BA-EX1F)
                                                    (SEQ ID NO: 21)
5' CGATCTCGGATCCCGTAACGGAATAGTCCACCCGGAT 3'

8-(X-Ex1 R)
                                                    (SEQ ID NO: 22)
5' CGGCAATGACCTCGAGACTCGACCTGCCTCGGCGTGTTTG 3'

9-(SAL-EX1F)
                                                    (SEQ ID NO: 23)
5' GGCGTCAATGTCGACCGTAACGGAATAGTCCACCCGGAT 3'

10-(ECORI-EX1R)
                                                    (SEQ ID NO: 24)
5' CGGACGTTGGAATTCGATCGACCTGCCTCGGCGTGTTTG 3'
```

PCR is carried out in 25 µl reaction in a condition of 2.5 µl PCR buffer; 1.5 µl MgCL (25 mM); 0.5 µl dNTPs (10 mM); each primer 0.5 µl (10 pmol/µl); 0.15 µl Taq DNA polymerase (5 U/µl); 10-40 ng DNA template. Thermal profile of PCR is [94° C./4; (94° C./30"; 59° C./30"; 72° C./45")×3; (94° C./30"; 57° C./30"; 72° C./45")×3; (94° C./30"; 54° C./30"; 72° C./45")×35; 72° C./10']. Afterward, these PCR products are also performed in the same manner with those have been done in *Aedes albopictus* and *Aedes polynesiensis*. Whatever, these fragments are connected by a linker or intron, after this RNAi kernel sequence (3) is constructed, it would be available to ligate into the transactivator plasmids to transform *Culex quinquesfaciatus* embryos.

III. Connection of the RNAi Kernel Structures with Tre Repressor.

The pTre-tight plasmid (Cat. No. 631059) from Clontech is mixed with the RNAi kernel sequence (1 or 2 or 3) in 1:3 molar ratio in a 30 µl reaction in the presence of BamHI and SalI restriction enzymes. After digestion, ligation is performed by adding T4 ligation into the denatured restriction enzyme mixture. The circle plasmid is transformed into competent cells (DH5α™ derivative, New England Biolabs), isolated and cultured overnight to harvest a larger amount of plasmid DNA from each clone. The size of new plasmid would be 2.6 kb plus the size of the RNAi kernel sequences. In the case of RRM1 and RRM2 from *Aedes albopictus* and *Aedes polynesiensis*, only 135 bp of each RRM are used, the plasmid size would be about 3070 bp if using an intron of 200 bp. If a linker of 10 bp is used, the plasmid is about 2870 bp. In the case of *Culex quinquesfaciatus*, whole 240 bp is used, if it is accompanied with 200 bp intron, the fragment size would be 3280 bp. If a linker of 10 bp is used, the plasmid is about 3090 bp.

A fragment includes the Tre operator and the RNAi kernel sequence (tetOx7+PminCMV+RNAi kernel sequence +SV40 polyA) can now be amplified by two primers which contain HindIII and Acc65I restriction sites. These pending sites are available for ligation with Piggybac plasmid and the other parts of the construct.

```
(Tre-HindIII) CGATCTAAGCTTCTCGAGTTTACTCCCTATCAGTGA    (SEQ ID NO: 25)

(Tre-Acc65I)  CGATCTGGTACCAGTCAGTGAGCGAGGAAGCTCGAG    (SEQ ID NO: 26)
```

IV. Connection of the *Drosophila* β2 Tubulin Promoter with a Transactivator Sequence.

*Drosophila* β2 tubulin promoter sequence is obtained from GenBank or http://flybase.org/reports/FBgn0003889.html. Two primers which contain EcoRI and Apa I are designed from the sequence. These primers amplify 230 bp of 5'UTR of β2 tubulin gene from *Drosophila* genomic DNA. Thermal profile of PCR is [94° C./4; (94° C./30"; 55° C./30"; 72° C./45")×35; 72° C./10'].

```
β2-Apa1-F
                                                    (SEQ ID NO: 27)
CGATCTGGGCCCGGAAATCGTAGTAGCCTATTTGTGA

β2-EcoRI-R
                                                    (SEQ ID NO: 28)
CGGACGTTGGAATTCCCTGAATGTGTACAATTTCACGCAT
```

The pTet-Off-Advanced plasmid (Clontech, Catalog Nos. 630934) is digested by two restriction enzymes EcoRI and HindIII producing a band of 1222 bp. This DNA fragment is then ligated to the β2 tubulin promoter sequence via the EcoRI restriction site to produce a fragment of 1458 bp. tTA protein is now controlled by β2 tubulin promoter. The ligation product is digested by ApaI and purified by Qiagen columns. The product is available for a final ligation.

V. Whole Plasmid Assembles.

pXL-BacII-ECFP plasmid from http://piggybac.bio.nd.edu/ is used to assemble all the above fragments into completed Tra-2 RNAi constructs. The pXL-BacII-ECFP plasmid carries a 3×P3 promoter which drives ECEP reporter gene. This reporter gene would be tissue specific expressed under the promoter. When mosquitoes are transformed with this marker, mosquito eyes would be fluorescently cyan color.

The pXL-BacII-ECFP plasmid is digested by ApaI and Acc65I and purified by Qiagen columns. The linear plasmid is 5390 bp. The plasmid is then mixed with Tre fragments (III), β2+tTA fragment (IV) in 1:3:3 molar ratio. T4 ligation is added into a 30 μl reaction. Ligation product is used to transform into competent cells. Ligation products are expected in a range of different sizes as follow:

For *Aedes albopictus* and *Aedes polynesiensis*, two plasmid containing 10 bp linker or 200 bp intron are 7723 bp and 7913 bp, respectively. Meanwhile, plasmids of *Culex quinquesfaciatus* would be 7933 bp and 8123 bp for 10 bp linker and 200 bp intron, respectively.

VI. Plasmid Injection and Transformant Selection.

The Tra-2 RNAi plasmids is mixed with a pBSII-IE1-orf (http://piggybac.bio.nd.edu/) helper plasmid. The helper produces transposase enzyme which helps Piggybac in the Tra-2 RNAi plasmids jumping into mosquito genome. A good concentration of the injection mixture would be 600 ng of the Tra-2 RNAi plasmid plus 400 ng of the helper per micro liter (μl) of 1× phosphate buffer. Mosquito eggs would be injected within 2 hrs after oviposition into egg posterior ends. After 4 days post injection, the eggs are submerged into tetracycline solution (0.008 g per litter). Go survivors would be kept to cross with wild type males or females. G1 larvae are screened under a stereo fluorescent microscope. Any fluorescent larva found that would be the transformant one and to be crossed to build transformant lines. These lines would be tested in Tet-on and Tet-off conditions to check sex ratio. Any line having maleness skew over 80% in Te-off condition would be kept for further analysis and for vector control applications.

INVENTION EFFECTS

The method exposed in this invention would help to produce one sex (maleness) in Culicinae mosquitoes. Males created by this invention would pass on the Tra-2 RNAi genetic system into natural population when being released. If the number of released males is big enough, it can result in a collapse of natural vector population, even gone extinct of whole population in a certain time.

SEQUENCE LISTING

```
<160> NUMBER OF SEQ ID NOS: 28

<210> SEQ ID NO 1
<211> LENGTH: 240
<212> TYPE: DNA
<213> ORGANISM: Aedes sp.
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (195)..(195)
<223> OTHER INFORMATION: a, c, t, g, unknown or other

<400> SEQUENCE: 1
agtaagtgcc tcggtgtgtt cggcctaagc agctacacca acgaaaccag cctgatggac      60
gttttcgcac cgtacggaac cattgacaag gcgatgattg tctacgatgc caagacgaag     120
gtttcccgng ggttcggatt cgtgtacttc caggagcaga gtgcggccac cgaagccaaa     180
atgcagtgya atggnatgat gctgcatgag cgcacgatta gagtggatta ttcggtgacc     240

<210> SEQ ID NO 2
```

<211> LENGTH: 240
<212> TYPE: DNA
<213> ORGANISM: Aedes sp.
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other

<400> SEQUENCE: 2

```
agtaagtgcc tcggtgtgtt cggcctnagy agctayacca mcgaarccar cctgatggay      60
gtnttckcnc cgtwcggnac cathgacaag gcnatgattg tctacgatgc caagacgaag     120
gyntcccgng ggttyggntt cgtgtayttc caggagcaga gtkcggccac ngargccaaa     180
mtgcagtgya ayggaatgrw rctgcaygag cgnacgatta gagtggatta ttcggtgacc     240
```

<210> SEQ ID NO 3
<211> LENGTH: 240
<212> TYPE: DNA
<213> ORGANISM: Culex quinquefasciatus

<400> SEQUENCE: 3

```
cgtaacggaa tagtccaccc ggatggttcg ctcgtgcatt accattccgt tgcactgcac      60
cttggctgcg gaagcgtcct ccaggttgac aaagtacacg aatccgaacc cgcgggacgc     120
cttcgtcttg gcatcgtaca cgatctgcac cttctcgatc aatccgaacc ggccaaacac     180
ggtcctcagg tccgcctcct gggtgtaatt gctgaggcca acacgccga ggcaggtcga      240
```

<210> SEQ ID NO 4
<211> LENGTH: 240
<212> TYPE: DNA
<213> ORGANISM: Aedes sp.
<220> FEATURE:
<221> NAME/KEY: modified_base
<222> LOCATION: (46)..(46)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other

<400> SEQUENCE: 4

```
ggtcaccgaa taatccactc taatcgtgcg ctcatgcagc atcatnccat tycactgcat    60
tttggcttcg gtggccgcac tctgctcctg gaagtacacg aatccgaacc cncgggaaac  120
cttcgtcttg gcatcgtaga caatcatcgc cttgtcaatg gttccgtacg gtgcgaaaac  180
gtccatcagg ctggtttcgt tggtgtagct gcttaggccg aacacaccga ggcacttact  240
```

<210> SEQ ID NO 5
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ser Lys Cys Leu Gly Val Phe Gly Leu Ser Ser Tyr Thr Asn Glu Thr
1               5                   10                  15

Ser Leu Met Asp Val Phe Ala Pro Tyr Gly Thr Ile Asp Lys Ala Met
            20                  25                  30

Ile Val Tyr Asp Ala Lys Thr Lys Val Ser Arg Gly Phe Gly Phe Val
        35                  40                  45

Tyr Phe Gln Glu Gln Ser Ala Ala Thr Glu Ala Lys Met Gln Cys Asn
    50                  55                  60

Gly Met Met Leu His Glu Arg Thr Ile Arg Val Asp Tyr Ser Val Thr
65                  70                  75                  80
```

<210> SEQ ID NO 6
<211> LENGTH: 240
<212> TYPE: DNA
<213> ORGANISM: Aedes sp.
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (103)..(103)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other
<220> FEATURE:
<221> NAME/KEY: modified_base
<222> LOCATION: (118)..(118)
<223> OTHER INFORMATION: a, c, t, g, unknown or other
<220> FEATURE:
<221> NAME/KEY: modified_base
<222> LOCATION: (148)..(148)
<223> OTHER INFORMATION: a, c, t, g, unknown or other
<220> FEATURE:
<221> NAME/KEY: modified_base
<222> LOCATION: (163)..(163)
<223> OTHER INFORMATION: a, c, t, g, unknown or other
<220> FEATURE:
<221> NAME/KEY: modified_base
<222> LOCATION: (172)..(172)
<223> OTHER INFORMATION: a, c, t, g, unknown or other
<220> FEATURE:

```
<221> NAME/KEY: modified_base
<222> LOCATION: (178)..(178)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other

<400> SEQUENCE: 6
ggtcaccgaa taatccactc taatcgtncg ctcytgcagr wrcattccyt tycactgcam      60
tttggcrtcn gtggccgkac tctgctcctg gaaytacacg aanccyaacc cncgggganyc   120 cttcgtcttg gcatcgtaga caatcatngc cttgtchatg gtnccgwacg gngkgaaanac   180 ytccatcagg rtggrttcgm tggtytagct yctnaggccg aacacaccga ggcacttact    240

<210> SEQ ID NO 7
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Lys Cys Leu Gly Val Phe Gly Leu Ser Ser Tyr Thr Thr Glu Thr
1               5                   10                  15

Asn Leu Met Asp Val Phe Ser Pro Phe Gly Thr Ile Asp Lys Ala Met
            20                  25                  30

Ile Val Tyr Asp Ala Lys Thr Lys Ala Ser Arg Gly Phe Gly Phe Val
        35                  40                  45

Tyr Phe Gln Glu Gln Ser Ser Ala Thr Glu Ala Lys Leu Gln Cys Asn
    50                  55                  60

Gly Met Glu Leu His Glu Arg Thr Ile Arg Val Asp Tyr Ser Val Thr
65                  70                  75                  80

<210> SEQ ID NO 8
<211> LENGTH: 240
<212> TYPE: DNA
<213> ORGANISM: Culex quinquefasciatus

<400> SEQUENCE: 8
tcgacctgcc tcggcgtgtt tggcctcagc aattacaccc aggaggcgga cctgaggacc      60
gtgtttggcc ggttcggatt gatcgagaag gtgcagatcg tgtacgatgc caagacgaag   120
gcgtcccgcg ggttcggatt cgtgtacttt gtcaacctgg aggacgcttc cgcagccaag   180
gtgcagtgca acggaatggt aatgcacgag cgaaccatcc gggtggacta ttccgttacg   240

<210> SEQ ID NO 9
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Thr Cys Leu Gly Val Phe Gly Leu Ser Asn Tyr Thr Gln Glu Ala
1               5                   10                  15

Asp Leu Arg Thr Val Phe Gly Arg Phe Gly Leu Ile Glu Lys Val Gln
            20                  25                  30

Ile Val Tyr Asp Ala Lys Thr Lys Ala Ser Arg Gly Phe Gly Phe Val
        35                  40                  45
```

```
Tyr Phe Val Asn Leu Glu Asp Ala Ser Ala Ala Lys Val Gln Cys Asn
         50                  55                  60

Gly Met Val Met His Glu Arg Thr Ile Arg Val Asp Tyr Ser Val Thr
 65                  70                  75                  80
```

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtaagtgcc tcggtgtgtt cggcct                                          26

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccggtcaccg aataatccac tcaa                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a, c, t, g, unknown or other

<400> SEQUENCE: 12
atgccaagac gaaggtttcc cgng                                            24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttagagtgga ttattcggtg acc                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 14
atgccaagac gaaggyntcc cgn                                            23

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgatctcgga tccatgccaa gacgaaggtt tcccgag                             37

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggcaatgac ctcgagaccg gtcaccgaat aatccactca a                        41

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggcgtcaatg tcgacatgcc aagacgaagg tttcccgag                           39

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cggacgttgg aattcgacgg tcaccgaata atccactcaa                          40

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgtaacggaa tagtccaccc ggat                                           24

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 20
caaacacgcc gaggcaggtc ga                                            22

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgatctcgga tcccgtaacg gaatagtcca cccggat                            37

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggcaatgac ctcgagactc gacctgcctc ggcgtgtttg                         40

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggcgtcaatg tcgaccgtaa cggaatagtc cacccggat                          39

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cggacgttgg aattcgatcg acctgcctcg gcgtgtttg                          39

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgatctaagc ttctcgagtt tactccctat cagtga                             36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgatctgggc ccggaaatcg tagtagccta tttgtga                            37

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cggacgttgg aattccctga atgtgtacaa tttcacgcat                         40
```

(preceding line: `cgatctggta ccagtcagtg agcgaggaag ctcgag    36`)

The invention claimed is:

1. A Tra-2 RNAi DNA construct comprising
(1) a RNAi kernel sequence selected from the group consisting of:
SEQ ID NO:1 connected by an intron or linker DNA sequence to SEQ ID NO:4, where the intron or linker DNA sequence is connected to the end of SEQ ID NO:1 via a GT sequence, and is connected to the beginning of SEQ ID NO:4 via an AG sequence,
SEQ ID NO:2 connected by an intron or linker DNA sequence to SEQ ID NO:6 via a GT sequence, where the intron or linker DNA sequence is connected to the end of SEQ ID NO:2 and the beginning of SEQ ID NO:6 via an AG sequence,
and
SEQ ID NO:3 connected by an intron or linker DNA sequence to SEQ ID NO:8 via a GT sequence, where the intron or linker DNA sequence is connected to the end of SEQ ID NO:3 and the beginning of SEQ ID NO:8 via an AG sequence
wherein the transcription of SEQ ID NO:1 and SEQ ID NO:4 produces a first set of single strands of mRNA with complementary sequences exposed at ends of the strands of mRNA, and wherein the transcription of SEQ ID NO:2 and SEQ ID NO:6 produces a second set of single strands of mRNA with complementary sequences exposed at ends of the strands of mRNA, and wherein the transcription of SEQ ID NO:3 and SEQ ID NO:8 produces a third set of single strands of mRNA with complementary sequences exposed at ends of the strands of mRNA, which first, second and third sets of single strands of mRNA each respectively have complementary sequences which are of sufficient length so as to be capable of binding together to form a double strand hairpin mRNA structure having a loop portion, where the loop portion is formed by the transcription product of the intron or linker DNA sequence,
(2) a tetracycline repressible transactivator operably linked and controlling expression of the RNAi kernel sequence, and
(3) an insect spermatogenesis promoter operably linked and controlling expression of the tetracycline repressible transactivator,
and wherein the Tra-2 RNAi DNA construct is capable of stable expression during spermatogenesis in a Culicinae mosquito transformed therewith, so that the double strand hairpin mRNA structure produced is effective for Tra-2 gene knockdown of X(m) chromosome-bearing sperms.

2. A DNA sequence comprising SEQ ID NO:1 connected by an intron or linker DNA sequence to SEQ ID NO:4, where the intron or linker DNA sequence is connected to the end of SEQ ID NO:1 via a GT sequence, and is connected to the beginning of SEQ ID NO:4 via an AG sequence.

3. A DNA sequence comprising SEQ ID NO:2 connected by an intron or linker DNA sequence to SEQ ID NO:6 via a GT sequence, where the intron or linker DNA sequence is connected to the end of SEQ ID NO:2 and the beginning of SEQ ID NO:6 via an AG sequence.

4. A DNA sequence comprising SEQ ID NO:3 connected by an intron or linker DNA sequence to SEQ ID NO:8 via a GT sequence, where the intron or linker DNA sequence is connected to the end of SEQ ID NO:3 and the beginning of SEQ ID NO:8 via an AG sequence.

5. A Tra-2 RNAi DNA construct comprising
(1) a RNAi kernel sequence comprising
a first DNA sequence is selected from the group consisting of SEQ ID NO:1, SEQ ID NO:2, and SEQ ID NO:3,
a second DNA sequence which is an inverted repeat of the first DNA sequence, and
an intron or a linker DNA sequence, which intron or linker DNA sequence is connected to the end of the first DNA sequence and the beginning of the second DNA sequence,
wherein the transcription of the first and second DNA sequences produces single strands of mRNA with complementary sequences exposed at ends of the strands of mRNA, which complementary sequences are of sufficient length so as to be capable of binding together to form a double strand hairpin mRNA structure having a loop portion, where the loop portion is formed by the transcription product of the intron or linker DNA sequence,
(2) a tetracycline repressible transactivator operably linked and controlling expression of the RNAi kernel sequence, and
(3) an insect spermatogenesis promoter operably linked and controlling expression of the tetracycline repressible transactivator,
and wherein the Tra-2 RNAi DNA construct is capable of stable expression during spermatogenesis in a Culicinae mosquito transformed therewith, so that the double strand hairpin mRNA structure produced is effective for Tra-2 gene knockdown of X(m) chromosome-bearing sperms.

* * * * *